(12) United States Patent
Marsh

(10) Patent No.: US 10,765,613 B2
(45) Date of Patent: Sep. 8, 2020

(54) STABLE LOTION EMULSION COMPOSITION AND WET WIPE

(71) Applicant: The Procter & Gamble Company, Cincinnati, OH (US)

(72) Inventor: Randall Glenn Marsh, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 14/867,059

(22) Filed: Sep. 28, 2015

(65) Prior Publication Data

US 2016/0089314 A1 Mar. 31, 2016

Related U.S. Application Data

(60) Provisional application No. 62/057,297, filed on Sep. 30, 2014.

(51) Int. Cl.
| | | |
|---|---|---|
| *A61K 8/37* | (2006.01) | |
| *A61K 8/06* | (2006.01) | |
| *A61K 8/73* | (2006.01) | |
| *A61K 8/49* | (2006.01) | |
| *A61K 8/368* | (2006.01) | |
| *A61K 8/02* | (2006.01) | |
| *A61Q 19/10* | (2006.01) | |
| *A61Q 19/00* | (2006.01) | |
| *B08B 1/00* | (2006.01) | |
| *A47K 10/32* | (2006.01) | |

(52) U.S. Cl.
CPC .............. *A61K 8/37* (2013.01); *A47K 10/32* (2013.01); *A61K 8/0208* (2013.01); *A61K 8/06* (2013.01); *A61K 8/368* (2013.01); *A61K 8/4973* (2013.01); *A61K 8/73* (2013.01); *A61Q 19/005* (2013.01); *A61Q 19/10* (2013.01); *B08B 1/006* (2013.01); *A47K 2010/3266* (2013.01); *A61K 2800/87* (2013.01)

(58) Field of Classification Search
None
See application file for complete search history.

(56) References Cited

U.S. PATENT DOCUMENTS

| | | |
|---|---|---|
| 3,967,756 A | 7/1976 | Barish |
| 3,982,659 A | 9/1976 | Ross |
| 3,986,479 A | 10/1976 | Bonk |
| 3,994,417 A | 11/1976 | Boedecker |
| 4,323,468 A | 4/1982 | Grollier |
| 4,471,881 A | 9/1984 | Foster |
| 4,840,270 A | 6/1989 | Caputo et al. |
| 4,971,220 A | 11/1990 | Kaufman et al. |
| 5,050,737 A | 9/1991 | Joslyn et al. |
| 5,143,679 A | 9/1992 | Weber et al. |
| 5,322,178 A | 6/1994 | Foos |
| 5,366,104 A | 11/1994 | Armstrong |
| 5,518,801 A | 5/1996 | Chappell et al. |
| 5,525,588 A * | 6/1996 | Michetti .............. A61K 8/06 512/4 |
| 5,628,097 A | 5/1997 | Curro et al. |
| 5,647,506 A | 7/1997 | Julius |
| 5,658,639 A | 8/1997 | Curro et al. |
| 5,785,179 A | 7/1998 | Buczwinski et al. |
| 5,791,465 A | 8/1998 | Niki et al. |
| 5,914,084 A | 6/1999 | Benson et al. |
| 5,916,661 A | 6/1999 | Curro et al. |
| D414,637 S | 10/1999 | Amundson et al. |
| D416,794 S | 11/1999 | Cormack |
| D421,901 S | 3/2000 | Hill |
| D421,902 S | 3/2000 | Hill |
| 6,092,690 A | 7/2000 | Bitowft et al. |
| 6,114,263 A | 9/2000 | Benson et al. |
| 6,129,801 A | 10/2000 | Benson et al. |
| D437,686 S | 2/2001 | Balzar et al. |
| D443,451 S | 6/2001 | Buck et al. |
| D443,508 S | 6/2001 | Braaten et al. |
| D445,329 S | 7/2001 | Zethoff |
| 6,269,969 B1 | 8/2001 | Huang et al. |
| 6,269,970 B1 | 8/2001 | Huang et al. |

(Continued)

FOREIGN PATENT DOCUMENTS

| | | |
|---|---|---|
| EP | 2243462 | 10/2010 |
| JP | H267247 | 3/1990 |

(Continued)

OTHER PUBLICATIONS

Kaß, et al., "Systemic investigations in the antimicrobial efficacy of glycerine esters with fatty acids of different chain length", INFORM, Jun. 2014, vol. 25 (6), pp. 390-393.
Pilz, Dr. Frederic, "Sorbitan Caprylate—the Preservative Boosting, Multifunctional Ingredient", Cosmetic Science Technology, 2011, p. 131.
"Velsan™ SC, Ingredient for the cosmetic industry" Clariant International Ltd., Division Functional Chemicals, Jun. 2010, 2 pages.
International Search Report, PCT/US2014/046473, dated Nov. 14, 2014, 12 pages.
International Search Report, PCT/US2015/052788, dated Dec. 14, 2015, 11 pages.

(Continued)

*Primary Examiner* — David J Blanchard
*Assistant Examiner* — Sarah J Chickos
(74) *Attorney, Agent, or Firm* — Daniel S. Albrecht; Kathleen Y. Carter

(57) ABSTRACT

A lotion emulsion composition comprising a preservative enhancing agent and a rheology modifier, wherein the preservative enhancing agent comprises one of sorbitan caprylate, glyceryl caprylate/caprate, or a combination thereof, the rheology modifier comprises a hydrocolloid, the pH of the lotion emulsion composition is less than about 4.2, and the combined amount of preservative enhancing agent and rheology modifier is less than about 0.3% by weight of the total lotion emulsion composition.

11 Claims, 4 Drawing Sheets

(56) References Cited

U.S. PATENT DOCUMENTS

| | | |
|---|---|---|
| 6,296,144 B1 | 10/2001 | Tanaka et al. |
| 6,315,114 B1 | 11/2001 | Keck et al. |
| D451,279 S | 12/2001 | Chin |
| 6,383,431 B1 | 5/2002 | Benson et al. |
| 6,401,968 B1 | 6/2002 | Huang et al. |
| 6,412,634 B1 | 7/2002 | Flaig et al. |
| 6,440,437 B1* | 8/2002 | Krzysik .............. A61K 8/0208 424/400 |
| 6,444,629 B1* | 9/2002 | Elliott ................. A61K 8/8111 510/119 |
| 7,005,557 B2 | 2/2006 | Klofta et al. |
| 7,037,569 B2 | 5/2006 | Curro et al. |
| 7,410,683 B2 | 8/2008 | Curro et al. |
| 7,553,532 B2 | 6/2009 | Turner et al. |
| 7,666,827 B2 | 2/2010 | Marsh et al. |
| 8,221,774 B2 | 7/2012 | Marsh et al. |
| 8,987,180 B2 | 3/2015 | Wenzel |
| 2002/0064323 A1 | 5/2002 | Chin |
| 2004/0091446 A1 | 5/2004 | Massaro |
| 2008/0311231 A1 | 12/2008 | Modak et al. |
| 2010/0158964 A1 | 6/2010 | Cunningham |
| 2011/0104085 A1 | 5/2011 | Klug et al. |
| 2011/0159074 A1 | 6/2011 | Warren et al. |
| 2011/0244199 A1* | 10/2011 | Brennan ............... D04H 3/005 428/196 |
| 2011/0268777 A1 | 11/2011 | Marsh et al. |
| 2012/0066852 A1 | 3/2012 | Trinkhaus et al. |
| 2012/0101135 A1* | 4/2012 | Klug ..................... A01N 37/06 514/345 |
| 2012/0245132 A1 | 9/2012 | Zeng |
| 2013/0022562 A1 | 1/2013 | Maunsell et al. |
| 2013/0039961 A1* | 2/2013 | Gonzales ............. A61K 8/8117 424/401 |
| 2014/0349902 A1 | 11/2014 | Allef et al. |
| 2015/0017218 A1 | 1/2015 | Pettigrew et al. |

FOREIGN PATENT DOCUMENTS

| | | |
|---|---|---|
| JP | 2007-320873 | 12/2007 |
| JP | 2008-100991 | 5/2008 |
| WO | WO 99/55213 | 11/1999 |
| WO | WO 00/27268 | 5/2000 |
| WO | WO 02/14172 | 2/2002 |
| WO | WO 2007/070795 A2 | 6/2007 |
| WO | WO 2008/129494 A1 | 10/2008 |

OTHER PUBLICATIONS

Pilz, F., Sorbitan Caprylate—A New Preservative for Formulations, SOFW Journal, vol. 38, pp. 32-36 (Aug. 2012).
12995M All Office Action, U.S. Appl. No. 14/330,171.

* cited by examiner

STABLE LOTION EMULSION COMPOSITION AND WET WIPE

FIELD

The present disclosure includes a lotion emulsion composition for use in a wet wipe. The lotion emulsion composition comprises a preservative system for limiting the growth of microbes.

BACKGROUND

Wet wipes are constructed from porous or absorbent sheets impregnated with a lotion and they are sold and stored in an air-tight container or wrapper to prevent the sheets drying out. Wet wipes are made for a variety of uses. The two main categories of use are firstly, those for general household cleaning tasks, such as the cleaning of hard surfaces like floors or kitchen surfaces and secondly, those made for personal cleansing, such as the removal of make-up, or the cleaning of infants prior to the fitting of a new diaper or the simple refreshment of the skin after meals or while traveling. Wipes have also found use with feminine health and adult incontinence products.

A major proportion of the wipes intended for the cleansing of human skin are wet wipes which are designed for use with infants and young children. They are particularly used by parents during the changing of babies to clear away any excess fecal or urine residues in the peri-anal region before applying a fresh diaper or nappy. Wet wipes are required to be effective at cleaning while at the same time being very gentle and mild on the skin of the baby. This is especially important given that the skin of the baby around the genitals and anus can become very sensitive or rash-prone after extended contact with urine and fecal matter.

The dual aim of providing effective cleaning while at the same time being mild on the skin is usually a balancing act for the manufactures of wet wipes. This is because the chemical compounds required for effective cleaning and preservation of the wet wipe are often those that are the least mild on human skin.

For regulatory approval for wet wipe products there are strict limits to the allowable growth of microbes within the lotion/substrate media. To reach these standards all wipe products to date have required some degree of preservation, from known preservative compounds.

It would be desirable to develop a mild wet wipe that meets the preservative system efficacy requirements for microbial growth and that provides an alternative to known irritating preservative compounds. It would also be desirable to develop a preserved, stable lotion emulsion composition that comprises very low levels of materials for gentleness on the skin while simultaneously delivering a faster lotion drying rate and improved skin feel, which are consumer-preferred attributes.

SUMMARY

Aspects of the present disclosure may include a lotion emulsion composition comprising a preservative enhancing agent and a rheology modifier, wherein:
 a. the preservative enhancing agent comprises one of sorbitan caprylate, glyceryl caprylate/caprate, or a combination thereof;
 b. the rheology modifier comprises a hydrocolloid;
 c. the pH of the lotion emulsion composition is less than about 4.2; and
 d. the combined amount of preservative enhancing agent and rheology modifier is less than about 0.3% by weight of the total lotion emulsion composition.

Another aspect of the present invention is that the lotion emulsion composition may provide a faster drying rate than conventional products.

Another aspect of the present invention is that the lotion emulsion composition may provide less tack than conventional products.

Further aspects of the present invention may include a wet wipe comprising or impregnated with the lotion emulsion composition or an article of commerce comprising a container housing one or more wet wipes comprising the lotion emulsion composition.

In the lotion emulsion compositions of the present invention, surprisingly, the preservative enhancing agent may provide sufficient emulsification of hydrophobic materials, for example perfumes or silicone-containing materials, such that the preservative system, with low levels of preservative enhancing agent, such as sorbitan caprylate or glyceryl caprylate/caprate, even with low levels of a rheology modifier such as xanthan gum, may form a stable system. Without being bound by theory, it is believed that a rheology modifier and a preservative enhancing agent, such as xanthan gum and sorbitan caprylate or glyceryl caprylate/caprate, work together to provide sufficient emulsification for the other hydrophobic ingredients in the lotion emulsion composition, even when used at low levels.

Further, in the lotion emulsion compositions of the present invention, surprisingly, the use of low levels of a rheology modifier and a preservative enhancing agent, such as xanthan gum and sorbitan caprylate or glyceryl caprylate/caprate, deliver a faster lotion drying rate and less tack. Without being bound by theory, it is believed that the low level of rheology modifier enables faster release of water vapor while the preservative enhancing agent simultaneously provides additional lubrication.

DETAILED DESCRIPTION

Figure 1:
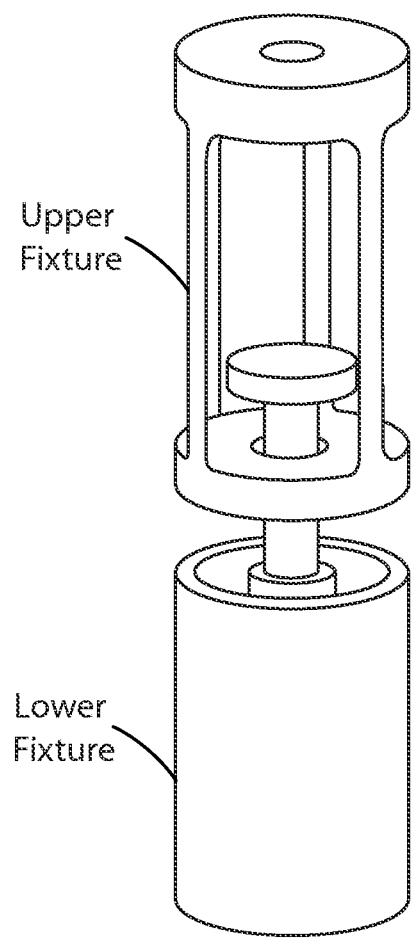
FIGS. 1, 2, 3, and 3A are drawings of a tack probe, which is part of the equipment that may be used to measure the average amount of tack exerted by a lotion emulsion composition while the lotion emulsion composition is drying on a defined surface.
Figure 2:
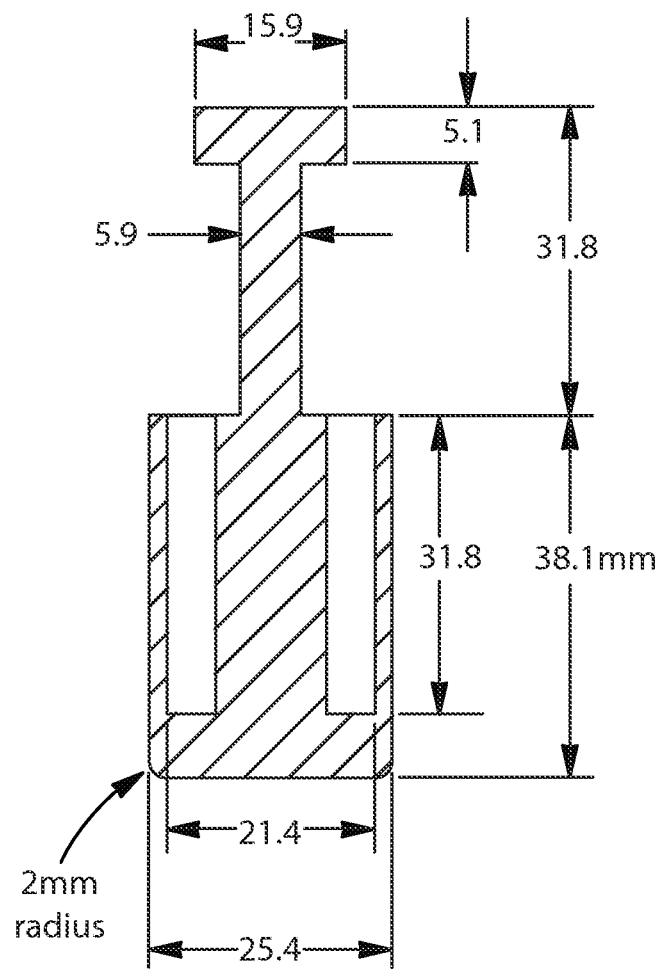
Figure 3:
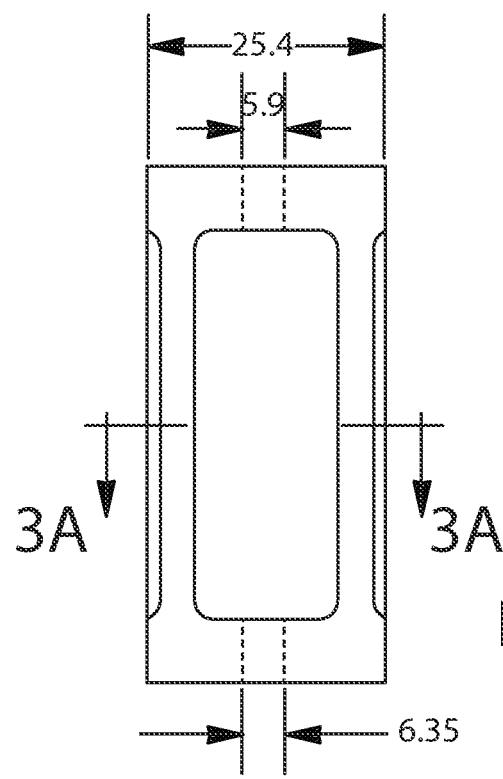
Figure 3A:
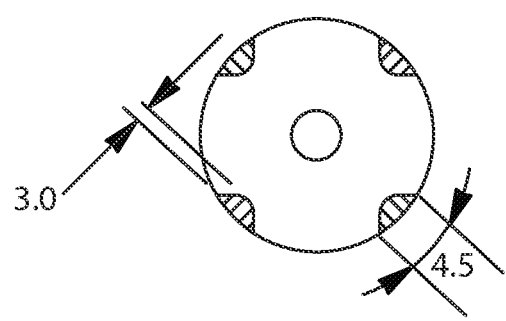

The following definitions may be useful in understanding the present disclosure:

"Soil" refers herein to matter that is extraneous to a surface being cleaned. For example, soils include body exudates, household matter, and outdoor matter. Body exudates include feces, menses, urine, vomitus, mucus, and the like. Household matter includes food, beverages, combinations thereof, and the like. Outdoor matter includes dirt, mud, snow, paint, crayons, and the like.

"Substrate" refers herein to a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes.

"Loading" refers to a process of applying a lotion emulsion composition to a substrate to form a wet wipe. A "loaded" substrate is associated with a lotion emulsion composition.

"Q.S." refers herein to "quantum sufficit" and is a sufficient percentage of water added to the composition to bring the overall composition to 100%.

As used herein, percentages are given as the weight of the component to the total weight of the lotion emulsion composition, unless otherwise indicated. Percentages reflect 100% active component material. For example, if a component is available in a dispersion at a concentration of 50% component to dispersion, by weight, twice as much of the dispersion, by weight, would be added to the lotion emulsion composition to provide the equivalent of 100% active component.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

While the present disclosure references the use of a wet wipe for cleaning skin, it is to be appreciated that the lotion emulsion composition of the present disclosure may be used with various substrates, including tissues, paper towel, toilet paper, and the like. The substrates may be directly loaded with a lotion emulsion composition or a lotion emulsion composition may be applied to the substrate at the time of use in the form of a liquid or spray. In addition, the substrates of the present disclosure may be used to clean various other surfaces other than skin, including countertops, walls, floors, and the like.

Lotion Emulsion Composition

Controlling microbiological growth may be beneficial in water-based products such as lotion emulsion compositions intended for use in wet wipes. The lotion emulsion composition may comprise a preservative system. In some exemplary configurations, the preservative system may include a preservative enhancing agent and one or more preservatives. A preservative may be understood to be a chemical or natural compound or a combination of compounds reducing the growth of microorganisms, thus enabling a longer shelf life for a package of substrates (opened or not opened) as well as creating an environment with reduced growth of microorganisms when transferred to the skin during the wiping process.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Low pH buffering systems, such as a citrate-citric acid buffering system at a pH of less than about 5, may also be employed as part of the preservative system. In some exemplary configurations, acidic compounds used in sufficient amount to reduce the pH of the lotion composition (e.g. pH of less than about 5) may be useful as a preservative, or as an enhancing agent for other preservative ingredients.

The lotion emulsion composition also includes a carrier such as water. The lotion emulsion composition may comprise greater than about 50%, greater than about 60%, greater than about 70%, greater than about 80%, greater than about 90%, greater than about 95%, greater than about 96%, or greater than about 97% by weight of water. The lotion emulsion composition may have a pH in the range of about 3 to about 5, or about 3.5 to about 4.2, or less than about 4. In addition, the lotion emulsion composition may include various optional ingredients, such as surfactants, emollients, film-formers, preservatives, pH buffers, rheology modifiers and the like, such as described in U.S. Pat. Nos. 7,666,827; 7,005,557; 8,221,774; and U.S. Patent Application Publication No. 2011/0268777. For example, the lotion emulsion composition may comprise optional ingredients such as perfumes, aloe, and chamomile.

Preservative Enhancing Agent

The preservative system may include one or more preservative enhancing agents. Exemplary preservative enhancing agents include sorbitan caprylate, glyceryl caprylate/caprate, or combinations thereof An exemplary sorbitan caprylate is manufactured by Clariant under the designation VELSAN® SC. An exemplary glyceryl caprylate/caprate may be CremerCOOR® GC810, CremerCOOR® GCB, or IMWITOR® 742, all available from Peter Cremer, or CAPMUL® 708G, available from Abitec.

The lotion emulsion composition may comprise from about 0.05% to about 0.29% by weight of a preservative enhancing agent. In some embodiments, the lotion emulsion composition may comprise at most about 0.2% by weight of a preservative enhancing agent.

Rheology Modifier

The lotion emulsion composition may comprise one or more rheology modifiers. A rheology modifier may help to stabilize the lotion emulsion composition by reducing or preventing coalescence of droplets of the hydrophobic materials in the composition.

Non-limiting examples of rheology modifiers include, but are not limited to, hydrocolloids, including natural gums, such as xanthan gum. Rheology modifiers, when present in the lotion emulsion composition, may be present in the range of about 0.01% to about 0.1% by weight, or about 0.06% by weight.

Preservative System

The preservative system of the lotion emulsion composition may comprise one or more preservative enhancing agents in combination with one or more preservatives. It has been found that a wet wipe having a lotion emulsion composition comprising a preservative enhancing agent and a preservative may have improved antimicrobial performance compared to a wet wipe having a lotion emulsion composition comprising a preservative without a preservative enhancing agent. As a result, lower concentrations of a preservative may be used in a lotion emulsion composition comprising a preservative enhancing agent than may be used when the lotion emulsion composition comprises a preservative without a preservative enhancing agent.

The lotion emulsion composition may include one or more preservatives. The preservative may include an organic acid or the salt thereof. Exemplary organic acids include benzoic acid or sorbic acid. Exemplary salts of organic acids include sodium benzoate and potassium sorbate, for example.

The lotion emulsion composition may comprise at most about 0.3%, or from about 0.05% to about 0.25% of a preservative. In some embodiments, the lotion emulsion composition may comprise from about 0.18% to 0.24% of a preservative.

The preservative system of the lotion emulsion composition may include additional compounds, for example chelating agents, such as ethylenediamine tetraacetic acid (EDTA) and its salts, or diethylene triamine pentaacetic acid (DTPA).

In some exemplary configurations, acidic compounds used in sufficient amount to reduce the pH of the lotion emulsion composition (e.g. pH of less than about 5) may be useful as a part of the preservative system. Low pH buffering systems, such as a citrate-citric acid buffering system, such as trisodium citrate and citric acid, at a pH of less than about 5, or less than about 4, may be employed as part of the preservative system.

An exemplary wet wipe may include a lotion emulsion composition comprising a preservative enhancing agent and a preservative. In an exemplary configuration, the lotion emulsion composition may comprise sorbitan caprylate and/or glyceryl caprylate/caprate and sodium benzoate. In a further exemplary configuration, the lotion emulsion composition may comprise sorbitan caprylate and/or glyceryl caprylate/caprate, sodium benzoate, EDTA, and a citrate-citric acid buffering system at a pH of less than about 4.

The lotion emulsion composition comprising a preservative enhancing agent and a preservative may be incorporated into a substrate at a load of about 200% to about 600% by weight of the substrate. In some exemplary configurations, a wet wipe comprising a substrate may comprise or be impregnated with the lotion emulsion composition with a lotion load of about 325% to 460%.

Optional Lotion Emulsion Composition Ingredients

Additional ingredients may be added to the lotion emulsion composition. The lotion emulsion composition may generally comprise any of the following ingredients: emollients, surfactants, rheology modifiers, or other adjunct ingredients such as texturizers, colorants, opacifying agents, soothing agents and medically active ingredients, such as healing actives and skin protectants. It is to be noted that some ingredient compounds can have a multiple function and that all compounds are not necessarily present in the lotion emulsion composition.

Emollient

The lotion emulsion composition may include an emollient. Emollients may (1) hydrate soil residues (for example, fecal residues or dried urine residues or menses residues), thus enhancing their removal from the skin, (2) hydrate the skin, thus reducing its dryness and irritation, (3) protect the skin from later irritation (for example, caused by the friction of an absorbent article) as the emollient is deposited onto the skin and remains at its surface as a thin protective layer, and (4) provide a desired sensory feel to the lotion emulsion composition and/or the skin.

An emollient may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

In some exemplary configurations, the lotion emulsion composition may comprise a mixture of caprylic/capric triglycerides in combination with Bis-PEG/PPG-16/16 PEG/PPG-16/16 dimethicone known as ABIL® CARE 85, available from Degussa Care Specialties.

Surfactant

The lotion emulsion composition may include one or more surfactants. The surfactant can be an individual surfactant or a mixture of surfactants. The surfactant may be a polymeric surfactant or a non-polymeric one. The surfactant or combinations of surfactants may be mild, which means that the surfactants provide sufficient cleaning or detersive benefits but do not overly dry or otherwise harm or damage the skin. The surfactant, when present in the lotion emulsion composition, may be present in an amount ranging from about 0.05% to about 1% by weight of the lotion emulsion composition.

In some exemplary configurations, the surfactant may comprise PEG-40 Hydrogenated Castor Oil, such as EMULSOGEN® HCW049 manufactured by Clariant.

Substrate

The lotion emulsion composition of the present disclosure may be loaded onto a substrate to form a wet wipe. The substrate may be a nonwoven material. The nonwoven material may comprise one or more layers of such fibrous assemblies, wherein each layer may include continuous fibers, coextruded fibers, non-continuous fibers and combinations thereof.

The fibers of the substrate may be comprised of any natural, cellulosic, and/or wholly synthetic material. Examples of natural fibers may include cellulosic natural fibers, such as fibers from hardwood sources, softwood sources, or other non-wood plants. The natural fibers may comprise cellulose, starch and combinations thereof. Non-limiting examples of suitable cellulosic natural fibers include wood pulp, typical northern softwood Kraft, typical southern softwood Kraft, typical CTMP, typical deinked, corn pulp, acacia, eucalyptus, aspen, reed pulp, birch, maple, radiata pine and combinations thereof. Other sources of natural fibers from plants include albardine, esparto, wheat, rice, corn, sugar cane, papyrus, jute, reed, sabia, raphia, bamboo, sidal, kenaf, abaca, sunn, rayon (also known as viscose), lyocell, cotton, hemp, flax, ramie and combinations thereof. Yet other natural fibers may include fibers from other natural non-plant sources, such as, down, feathers, silk, cotton and combinations thereof. The natural fibers may be treated or otherwise modified mechanically or chemically to provide desired characteristics or may be in a form that is generally similar to the form in which they can be found in nature. Mechanical and/or chemical manipulation of natural fibers does not exclude them from what are considered natural fibers with respect to the development described herein.

The synthetic fibers can be any material, such as those selected from the group consisting of polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof. Further, the synthetic fibers can be a single component (i.e., single synthetic material or mixture makes up entire fiber), bi-component (i.e., the fiber is divided into regions, the regions including two or more different synthetic materials or mixtures thereof and may include coextruded fibers and core and sheath fibers) and combinations thereof. Bicomponent fibers can be used as a component fiber of the structure, and/or they may be present to act as a binder for the other fibers present in the fibrous structure. Any or all of the synthetic fibers may be treated before, during, or after manufacture to change any desired properties of the fibers. The substrate may comprise hydrophilic fibers, hydrophobic fibers, or a combination thereof.

The substrate may comprise various percentages of natural and/or synthetic fibers. For example, in some exemplary configurations, the substrate may comprise 100% synthetic fibers. In another exemplary configuration, the substrate may comprise natural and synthetic fibers. For example, the substrate may comprise from about 0% to about 90% natural fibers, with the balance comprising synthetic fibers. The substrate may be comprised of 10%, 20%, 30%, 40%, 50%, 60%, 70%, or 80% natural fibers.

In certain configurations, it may be desirable to have particular combinations of fibers to provide desired characteristics. For example, it may be desirable to have fibers of certain lengths, widths, coarseness or other characteristics combined in certain layers, or separate from each other.

The fibers may be of virtually any size and may have an average length from about 1 mm to about 60 mm. Average fiber length refers to the length of the individual fibers if straightened out. The fibers may have an average fiber width of greater than about 5 micrometers. The fibers may have an average fiber width of from about 5 micrometers to about 50 micrometers. The fibers may have a coarseness of greater than about 5 mg/100 m. The fibers may have a coarseness of from about 5 mg/100 m to about 75 mg/100 m.

The fibers may be circular in cross-section, dog-bone shape, delta (i.e., triangular cross section), trilobal, ribbon, or other shapes typically produced as staple fibers. Likewise, the fibers can be conjugate fibers such as bicomponent fibers. The fibers may be crimped and may have a finish, such as a lubricant, applied.

The substrate materials may also be treated to improve the softness and texture thereof. The substrate may be subjected to various treatments, such as physical treatment, hydro-molding, hydro-embossing, and ring rolling, as described in U.S. Pat. No. 5,143,679; structural elongation, as described in U.S. Pat. No. 5,518,801; consolidation, as described in U.S. Pat. Nos. 5,914,084; 6,114,263; 6,129,801 and 6,383,431; stretch aperturing, as described in U.S. Pat. Nos. 5,628,097; 5,658,639; and 5,916,661; differential elongation, as described in U.S. Pat. No. 7,037,569, and other solid state formation technologies as described in U.S. Pat. Nos. 7,553,532 and 7,410,683; zone activation, and the like; chemical treatment, such as rendering part or all of the substrate hydrophobic, and/or hydrophilic, and the like; thermal treatment, such as thermal-embossing, softening of fibers by heating, thermal bonding and the like; and combinations thereof.

Without wishing to be bound by theory, it is believed that a textured substrate may further enable the ease of removal of soils by improving the ability to grip or otherwise lift the soils from the surface during cleansing. Any one of a number of texture elements may be useful in improving the ability to grip or otherwise lift the soil from the surface during cleansing such as continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, and the like, and combinations thereof. The texture elements may be hollow elements. The texture elements may be connected to each other. The texture elements may overlap each other.

The substrate may have a basis weight between about 15, 30, 40, or 45 grams/m$^2$ and about 65, 75, 85, 95, or 100 grams/m$^2$. A suitable substrate may be a carded nonwoven comprising a 40/60 blend of viscose fibers and polypropylene fibers having a basis weight of 58 grams/m$^2$ as available from Suominen of Tampere, Finland as FIBRELLA® 3160. FIBRELLA® 3160 is a 58 grams/m$^2$ nonwoven web comprising 60% by weight of 1.5 denier polypropylene fibers and 40% by weight of 1.5 denier viscose fibers. Another suitable material may be FIBRELLA® 3100 which is a 62 grams/m$^2$ nonwoven web comprising 50% by weight of 1.5 denier polypropylene fibers and 50% by weight of 1.5 denier viscose fibers. In both of these commercially available fibrous webs, the average fiber length is about 38 mm. Another suitable material for use as a substrate may be SAWATEX® 2642 as available from Sandler AG of Schwarzenbach/Salle, Germany. Yet another suitable material for use as a substrate may have a basis weight of from about 50 grams/m$^2$ to about 60 grams/m$^2$ and have a 20/80 blend of viscose fibers and polypropylene fibers. The substrate may also be a 60/40 blend of pulp and viscose fibers. Exemplary nonwoven substrates are described in U.S. Patent Publication 2012/066852 and U.S. Patent Publication U.S. 2011/244199.

In some configurations, the surface of the substrate may be essentially flat. In other configurations, the surface of the substrate may optionally contain raised and/or lowered portions. The raised and/or lowered portions can be in the form of logos, indicia, trademarks, geometric patterns, and/or images of the surfaces that the substrate is intended to clean (i.e., infant's body, face, etc.). The raised and/or lowered portions may be randomly arranged on the surface of the substrate or be in a repetitive pattern of some form.

In yet other configurations, the substrate may be biodegradable. For example, the substrate could be made from a biodegradable material such as a polyesteramide, or a high wet strength cellulose. In some exemplary configurations, the substrate may be dispersible.

Article of Commerce

In one embodiment, an article of commerce may be provided. The article of commerce may comprise a container and at least one wet wipe as described herein.

Containers may include, but are not limited to, PET tubs, flow wrap pouches, and other packaging known in the art as suitable for nonwoven articles. Additionally, the container may also be manufactured to facilitate removal of individual wet wipes.

The container may be made of any suitable material or materials and can be manufactured in any suitable manner.

For example, the container can be made of polystyrene, polypropylene, PET, POET, polyethylene, polyester, polyvinyl alcohol, or the like. The containers may also be made of a mixture of the above materials. The containers may be manufactured by, for example, a vacuum molding process or an injection molding process, or any suitable process.

Additional information on containers, as well as additional optional components for containers, including, but not limited to: container bodies, lids, container features, such as, but not limited to, attachment of lids, hinges, zippers, securing aids, and the like, can be found in U.S. Pat. Nos. Des. 451,279; Des. 437,686; Des. 443,508; Des 443,451; Des 421,901; Des 421,902; Des 416,794; Des 414,637; Des 445,329; 3,982,659; 3,967,756; 3,986,479; 3,994,417; 6,269,970; 5,785,179; 5,366,104; 5,322,178; 5,050,737; 4,971,220; 6,296,144; 6,315,114; 4,840,270; 4,471,881; 5,647,506; 6,401,968; 6,269,969; 6,412,634; 5,791,465; 6,092,690; U.S. Patent Application Publication No. 2002/0064323 published on May 30, 2002, issued to Chin; and WO 00/27268 published on May 18, 2000 and assigned to The Procter & Gamble Company; WO 02/14172 published on Feb. 21, 2002 and assigned to The Procter & Gamble Company; and WO 99/55213 published on Nov. 4, 1999 and assigned to The Procter & Gamble Company.

Lotion Stability Test Method

This method may be used for determining the stability of a lotion emulsion composition. Per ASTM D3707-89 Test Method B, a 100 ml sample of a lotion emulsion composition is placed in a graduated 100 ml cylinder, then incubated for 96 hours in a convection oven maintained at 85±1° C. After incubation, the cylinder is removed from the oven and allowed to stand at room temperature for a period of 1 hour. A lotion emulsion composition is determined to be unstable when a visually observable layer of material is floating at the top of it, indicating that the oily material in the lotion emulsion composition has separated. Quantifying the volume of oil and water separation, or upper layer and lower layer water content, as outlined in ASTM D3707-89, is not required.

Lotion Drying Rate Method

This method may be used for measuring the average drying rate of a lotion emulsion composition. Per ASTM E1868-10, a thermogravimetric analyzer, such as a TGA Q500 made by TA Instruments, capable of continuously recording specimen mass and temperature as a function of time, is used to measure the specimen mass rate of change. The furnace and flow parameters for the analyzer are set to 37° C. isothermal and 100 ml/min of bone-dry nitrogen, respectively. A 10 mg sample of a lotion emulsion composition is placed into the specimen holder and the mass of the specimen is recorded. Once the specimen reaches the test temperature, the analyzer sets this time as time zero for the experiment. The mass of the specimen is then recorded every 2.5 min for a total duration of 30 min, at which time the experiment is terminated. The experiment is repeated 3 times per sample type, and the average percent mass loss per time interval is calculated and reported. The drying rate is then calculated by determining the average specimen mass rate of change (in % mass/min) from time zero to time 10 min. An illustrative example is provided:

| | Time (min) | | | | |
|---|---|---|---|---|---|
| | 0 | 2.5 | 5 | 7.5 | 10 |
| Percent Mass Remaining Repeat 1 | 79.82 | 63.35 | 47.85 | 33.70 | 20.94 |
| Percent Mass Remaining Repeat 2 | 80.77 | 64.85 | 41.89 | 36.10 | 23.22 |
| Percent Mass Remaining Repeat 3 | 79.27 | 62.23 | 46.44 | 32.02 | 19.32 |
| Average Percent Mass Remaining (MR) | 79.95 | 63.48 | 45.39 | 33.94 | 21.16 |

$$\text{Lotion Drying Rate}(\% \text{ mass/min}) = \frac{\text{Avg \% MR Time Zero} - \text{Avg \% MR Time 10 Min}}{\text{Time Interval(Min)}}$$

$$\text{Lotion Drying Rate}(\% \text{ mass/min}) = \frac{79.95 - 21.16}{10} = 5.88$$

Lotion Tack Method

This method may be used for measuring the average amount of tack exerted by a lotion emulsion composition while the lotion emulsion composition is drying on a defined surface.

Figure 4:
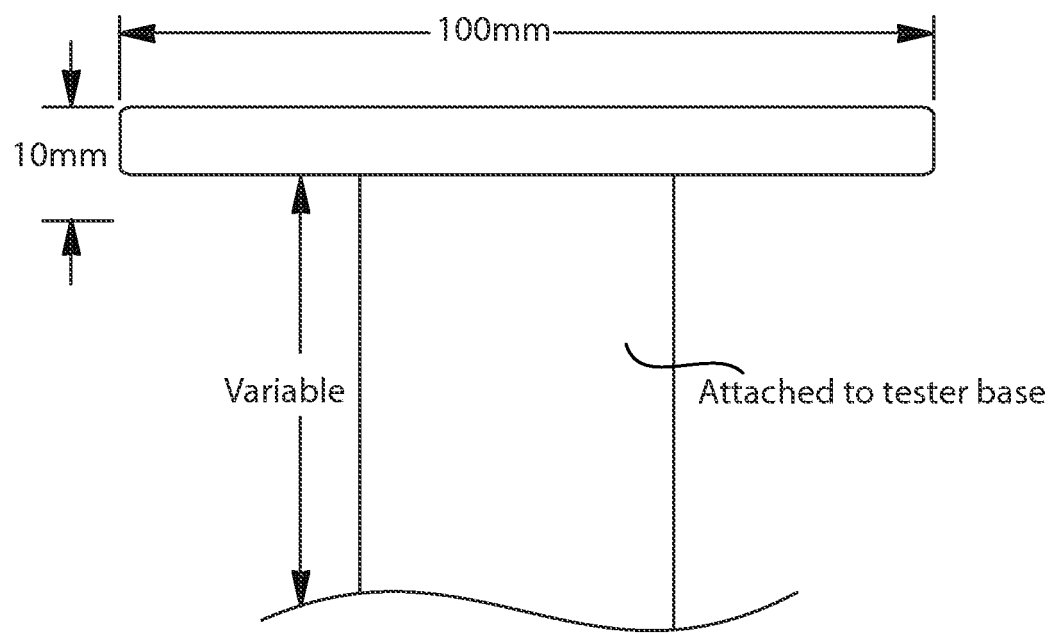
FIG. 4 is a drawing of a base platform, which is part of the equipment that may be used to measure the average amount of tack exerted by a lotion emulsion composition while the lotion emulsion composition is drying on a defined surface.

Tack is measured using a rate of extension tensile tester with computer interface (a suitable instrument is the MTS Insight using Testworks 4.0 Software, as available from MTS Systems Corp., Eden Prairie, Minn.) using a load cell for which the forces measured are within 1% to 90% of the limit of the cell. The Tack Probe (see FIGS. 1 through 3A) is fixed to the load cell. The lower section of the Tack Probe must have a mass of 16.5 g±0.5 g. A Base Platform (see FIG. 4) is attached to the tensile tester base. All testing is performed in a conditioned room maintained at about 23±2° C. and about 50±2% relative humidity.

The tensile tester is programmed to perform an extension/compression test, collecting force and extension data at an acquisition rate of 200 Hz as the crosshead rises at a rate of 5 mm/sec for 50 cycles. The Tack Probe is lowered until the lower section is just starting to rest under its own weight, unsupported by the upper section. At that point, the Tack Probe is raised 1 mm. In the pre-load step, the Tack Probe must descend at 13 mm/min until 5 grams of force is applied to the sample. After the pre-load step, the Tack Probe must descend a further 6 mm then stop and instantaneously ascend 9 mm, thus lifting the Tack Probe 3 mm above the surface of the sample. This is repeated for the 50 cycles.

All samples being tested must be conditioned at 23±2° C. and 50±2% relative humidity for at least 24 hours prior to testing. Each test specimen consists of two surfaces consisting of two 28.5 mm discs of copy paper (such as Staples® Multiuse Paper, 20 lb, 92 Bright, 8½"×11", 5,000/Case, Item: 818051, Model: DPS08511 as available from Staples.com, Diversity Product Solutions). The copy paper discs are adhered to the underside of the Lower Fixture in FIG. 1 and the upper surface of the Base Platform in FIG. 4, using double-sided tape (such as Double-Coated Tape 592 as available from Intertape Polymer group). Affix a copy paper disc to the center of the base of the Tack Probe. Fold the excess disc up around the edges of the base. Affix another copy paper disc to the center of the Base Platform. The Tack Probe and Base Platform must share a single perpendicular center point. Raise the upper section of the Tack Probe until a gap exists between the Lower Fixture of the Tack Probe and the Base Platform and, using a micro-pipettor (such as a Rainin Classic PR-100 as available from Mettler-Toledo Rainin Instrument LLC), deposit 30 μL of the lotion emulsion composition in the center of the copy paper disc on the Base Platform.

Start the test and collect data. The maximum force required to separate the two discs of copy paper is collected every cycle. For each lotion emulsion composition type, repeat the test at least 5 times using a new pair of paper discs each time. Calculate the average maximum separation force (in grams) for each cycle. The average maximum separation force at 25 cycles is used as the average measurement of tack exerted by a lotion emulsion composition while drying.

Examples

In the lotion emulsion compositions of the present invention, surprisingly, the preservative enhancing agent may provide sufficient emulsification of hydrophobic materials, for example perfumes or silicone-containing materials, such that the preservative system, with low levels of preservative enhancing agent, such as sorbitan caprylate or glyceryl caprylate/caprate, even with low levels of a rheology modifier such as xanthan gum, may form a stable system. Further, in the lotion emulsion compositions of the present invention, surprisingly, the use of low levels of a rheology modifier and a preservative enhancing agent, such as xanthan gum and sorbitan caprylate or glyceryl caprylate/caprate, deliver a faster lotion drying rate and less tack.

The following examples are illustrative, non-limiting lotion emulsion compositions that demonstrate the unique ability of lotion emulsion compositions of the present invention to form a stable system that simultaneously dries faster and has reduced tack.

Example 1 is an exemplary lotion emulsion composition of the present invention. It comprises a low concentration of xanthan gum in combination with a low level of preservative enhancing agent, delivering a stable system (as determined by the Lotion Stability Test Method) with a fast drying rate of 6.61% mass/min and a low tack of 15.5 grams (as determined by the Lotion Drying Rate Method and the Lotion Tack Method, respectively). In comparison, Example 2, which comprises a higher concentration of xanthan gum, while also delivering a stable system, has a slower drying rate of 5.88% mass/min and a higher tack of 36.1 grams. Also in comparison, Example 3, which comprises a lower concentration of Xanthan Gum, fails to deliver a stable system.

| Ex. | Lotion Compositions Ingredients | % w/w | Lotion Stability | Lotion Drying Rate (% mass/min) | Lotion Tackiness (grams) |
|---|---|---|---|---|---|
| 1 | Water | Q.S. | Stable | 6.61 | 15.5 |
|   | Disodium EDTA | 0.10 | | | |
|   | Sodium Benzoate | 0.24 | | | |
|   | Xanthan Gum* | 0.06 | | | |
|   | PEG-40 Hydrogenated Castor Oil | 0.44 | | | |
|   | BIS-PEG/PPG-16/16 PEG/PPG-16/16 Dimethicone Caprylic Capric Triglyceride† | 0.45 | | | |
|   | Preservative Enhancing Agent□ | 0.20 | | | |
|   | Citric Acid | 0.53 | | | |
|   | Trisodium Citrate | 0.33 | | | |
|   | Perfume | 0.14 | | | |
| 2 | Water | Q.S. | Stable | 5.88 | 36.1 |
|   | Disodium EDTA | 0.10 | | | |
|   | Sodium Benzoate | 0.24 | | | |
|   | Xanthan Gum* | 0.18 | | | |
|   | PEG-40 Hydrogenated Castor Oil | 0.44 | | | |
|   | BIS-PEG/PPG-16/16 PEG/PPG-16/16 Dimethicone Caprylic Capric Triglyceride† | 0.45 | | | |
|   | Preservative Enhancing Agent□ | 0.20 | | | |
|   | Citric Acid | 0.53 | | | |
|   | Trisodium Citrate | 0.33 | | | |
|   | Perfume | 0.14 | | | |
| 3 | Water | Q.S. | Unstable | NA | NA |
|   | Disodium EDTA | 0.10 | | | |
|   | Sodium Benzoate | 0.24 | | | |
|   | Xanthan Gum* | 0.00 | | | |
|   | PEG-40 Hydrogenated Castor Oil | 0.44 | | | |
|   | BIS-PEG/PPG-16/16 PEG/PPG-16/16 Dimethicone Caprylic Capric Triglyceride† | 0.45 | | | |
|   | Preservative Enhancing Agent□ | 0.20 | | | |
|   | Citric Acid | 0.53 | | | |
|   | Trisodium Citrate | 0.33 | | | |
|   | Perfume | 0.14 | | | |

*Xanthan FG as supplied by Jungbunzlauer, Austria.
†Abil Care 85 as supplied by Evonik Goldschmidt Corp, Hopewell, Virginia.
□Sorbitan caprylate or glyceryl caprylate/caprate as supplied by Clariant under the designation VELSAN ® SC, by Peter Cremer under the designation CremerCOOR ® GC810, CremerCOOR ® GC8, or IMWITOR ® 742, or by Abitec under the designation CAPMUL ® 708G.

Examples 4 and 5 represent lotion emulsion compositions comprising a preservative system that lacks a preservative enhancing agent as taught in the present invention. These two examples show that achieving a stable lotion emulsion composition with a low level of preservative and with a fast drying rate and low tack are not easily achieved.

| Ex. | Lotion Compositions Ingredients | % w/w | Lotion Stability | Lotion Drying Rate (% mass/min) | Lotion Tackiness (grams) |
|---|---|---|---|---|---|
| 4 | Water | Q.S. | Stable | 5.78 | 39.4 |
|   | Disodium EDTA | 0.10 | | | |
|   | Sodium Benzoate | 0.12 | | | |
|   | Xanthan Gum* | 0.18 | | | |
|   | PEG-40 Hydrogenated Castor Oil | 0.44 | | | |
|   | BIS-PEG/PPG-16/16 PEG/PPG-16/16 Dimethicone Caprylic Capric Triglyceride† | 0.45 | | | |
|   | Phenoxyethanol/Ethylhexylglycerin | 0.30 | | | |
|   | Benzyl Alcohol | 0.30 | | | |
|   | Citric Acid | 0.53 | | | |
|   | Trisodium Citrate | 0.33 | | | |
|   | Perfume | 0.14 | | | |
| 5 | Water | Q.S. | Unstable | NA | NA |
|   | Disodium EDTA | 0.10 | | | |
|   | Sodium Benzoate | 0.12 | | | |
|   | Xanthan Gum* | 0.06 | | | |
|   | PEG-40 Hydrogenated Castor Oil | 0.44 | | | |
|   | BIS-PEG/PPG-16/16 PEG/PPG-16/16 Dimethicone Caprylic Capric Triglyceride† | 0.45 | | | |
|   | Phenoxyethanol/Ethylhexylglycerin | 0.30 | | | |
|   | Benzyl Alcohol | 0.30 | | | |
|   | Citric Acid | 0.53 | | | |
|   | Trisodium Citrate | 0.33 | | | |
|   | Perfume | 0.14 | | | |

Collectively, these examples demonstrate that the unique combination of a preservative enhancing agent, such as sorbitan caprylate or glyceryl caprylate/caprate, in combination with a low level of a rheology modifier, such as xanthan gum, enables a lotion emulsion composition that is stable, that dries more quickly, that has reduced tack, and that comprises less than about 0.3% by weight of a preservative enhancing agent and a rheology modifier for gentleness.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising a substrate and a lotion emulsion composition; the lotion emulsion composition comprising from about 0.05% to about 0.29% of a preservative enhancing agent and from about 0.01% to about 0.06% of a rheology modifier, wherein:
   a. the preservative enhancing agent is sorbitan caprylate and/or glyceryl caprylate/caprate;
   b. the rheology modifier is xanthan gum
   c. the pH of the lotion emulsion composition is less than about 4.2;
   d. the combined amount of preservative enhancing agent and rheology modifier is less than about 0.3% by weight of the total lotion emulsion composition; and
   e. the lotion emulsion composition comprises greater than about 97% water;
   wherein the substrate comprises at least 70% synthetic fibers, by weight of the substrate, and at least 20% natural fibers, by weight of the substrate;
   wherein the synthetic fibers are selected from the group consisting of polyethylene terephthalate, polypropylene, and combinations thereof; and
   wherein the lotion has an average drying rate of greater than about 6.5% mass/min based on the Lotion Drying Rate Method.

2. The wet wipe of claim 1, wherein the lotion emulsion composition is stable based on the Lotion Stability Test Method.

3. The wet wipe of claim 1, wherein the amount of rheology modifier is about 0.06% by weight of the lotion.

4. The wet wipe of claim 1, wherein the amount of preservative enhancing agent is about 0.2% by weight of the lotion.

5. The wet wipe of claim 1, further comprising a perfume.

6. The wet wipe of claim 1, further comprising an emollient.

7. The wet wipe of claim 1, further comprising a chelating agent.

8. The wet wipe of claim 1, further comprising an organic acid or a salt of an organic acid.

9. The wet wipe of claim 8, wherein the salt of the organic acid is sodium benzoate.

10. An article of commerce comprising a container housing one or more of said wet wipes of claim 1.

11. A method of cleaning the skin comprising the step of contacting said skin with said wet wipe of claim 1.

* * * * *